(12) United States Patent
Sasaki et al.

(10) Patent No.: US 7,495,122 B2
(45) Date of Patent: Feb. 24, 2009

(54) HEAVY-HYDROGENATED NORBORNYL (METH)ACRYLATES, PROCESS FOR PRODUCING THEM, POLYMERS THEREOF AND OPTICAL MEMBERS

(75) Inventors: Hiroki Sasaki, Kanagawa (JP); Tsuneaki Maesawa, Saitama (JP); Nobuhiro Ito, Saitama (JP); Kazushige Muto, Saitama (JP)

(73) Assignees: Wako Pure Chemical Industries, Osaka (JP); Fujifilm Corporation, Tokyo (JP)

( * ) Notice: Subject to any disclaimer, the term of this patent is extended or adjusted under 35 U.S.C. 154(b) by 0 days.

(21) Appl. No.: 10/565,648

(22) PCT Filed: Jul. 23, 2004

(86) PCT No.: PCT/JP2004/010869

§ 371 (c)(1), (2), (4) Date: Jul. 11, 2006

(87) PCT Pub. No.: WO2005/010061

PCT Pub. Date: Feb. 3, 2005

(65) Prior Publication Data

US 2007/0027279 A1 Feb. 1, 2007

(30) Foreign Application Priority Data

Jul. 24, 2003 (JP) ............................. 2003-278951

(51) Int. Cl.
C07C 67/14 (2006.01)
C07C 69/74 (2006.01)

(52) U.S. Cl. ...................................... 560/114; 560/116

(58) Field of Classification Search ................ 560/114, 560/116
See application file for complete search history.

(56) References Cited

U.S. PATENT DOCUMENTS

| | | | |
|---|---|---|---|
| 4,732,716 A * | 3/1988 | Sakunaga et al. .......... 264/1.28 |
| 4,874,890 A * | 10/1989 | Kato et al. ................. 560/256 |
| 4,986,648 A * | 1/1991 | Kobayashi et al. ...... 351/160 R |
| 5,767,200 A * | 6/1998 | Koike ........................ 525/265 |
| 6,632,585 B1 | 10/2003 | Nakamura | |
| 2005/0177015 A1 * | 8/2005 | Hirota et al. ................ 585/400 |
| 2006/0025596 A1 | 2/2006 | Ito et al. | |
| 2006/0116535 A1 * | 6/2006 | Ito et al. ..................... 568/817 |

FOREIGN PATENT DOCUMENTS

| | | |
|---|---|---|
| CA | 962283 | 2/1975 |
| CA | 1303626 C | 6/1992 |
| DE | 3639117 A1 | 5/1988 |
| EP | 0268192 A2 | 5/1988 |
| EP | 1154323 A1 | 11/2001 |
| EP | 1535889 A1 | 6/2005 |
| EP | 1577280 A1 | 9/2005 |
| JP | 63-130563 | 6/1988 |
| JP | 8-179389 | 7/1996 |
| JP | 9-197148 | 7/1997 |
| JP | 9-235322 | 9/1997 |
| WO | WO 01/37049 A1 | 5/2001 |
| WO | WO 2004/022614 A2 | 3/2004 |

OTHER PUBLICATIONS

An Supplementary European Search Report form the EPO dated Oct. 17, 2008.

* cited by examiner

*Primary Examiner*—Vasu Jagannathan
*Assistant Examiner*—Karuna P Reddy
(74) *Attorney, Agent, or Firm*—Sughrue Mion, PLLC

(57) ABSTRACT

A novel compound represented by a formula [1] wherein $R^1$ and $R^2$ respectively represent a light or heavy hydrogen atom, $R^3$ represents a light or heavy hydrogen atom or a methyl group in which tree hydrogen atoms are respectively light or heavy hydrogen atoms, and $R^4$ is a norbornyl group provided that four or more hydrogen atoms in the norbornyl group are heavy hydrogen atoms; and a novel polymer produced by polymerization of a composition comprising the compound are disclosed.

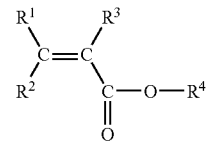

[1]

2 Claims, 1 Drawing Sheet

HEAVY-HYDROGENATED NORBORNYL (METH)ACRYLATES, PROCESS FOR PRODUCING THEM, POLYMERS THEREOF AND OPTICAL MEMBERS

TECHNICAL FIELD

The present invention relates to novel heavy-hydrogenated (meth)acrylates, especially relates to heavy-hydrogenated (meth) acrylates useful as material for optical fibers which are excellent in thermostability and transparency; and also relates to polymers produced by using them.

RELATED ARTS

It has been known that copolymer of norbornyl (meth) acrylate which is partially heavy-hydrogenated and heavy-hydrogenated methyl methacrylate are useful as a raw polymer for optical fibers. However the partially-heavy-hydrogenated norbornyl (meth) acrylate, which has been used as material for optical fibers, has a low heavy-hydrogenation content as a whole, and still contains many C—H bonds. And therefore, the copolymer produced by copolymerization of such partially-heavy-hydrogenated norbornyl (meth) acrylate and heavy-hydrogenated methyl methacrylate, which are disclosed in JPA No. syo 63-130563 (1988-130563) (the term "JPA" as used herein means an "unexamined published Japanese patent application), may thus give low transparency at a particular wavelength and the copolymer has large propagating-light loss at a particular wavelength when it is used as a raw material for optical fibers. Accordingly, it is required to provide heavy-hydrogenated norbornyl (meth) acrylate with a higher heavy-hydrogenation content.

An object of the present invention is to provide heavy-hydrogenated norbornyl (meth) acrylates with a high heavy-hydrogenation content, capable of being produced at low cost industrially, and to provide polymers which can be produced by using such norbornyl (meth) acrylates. And another object of the present invention is to provide heavy-hydrogenated norbornyl (meth) acrylates with a high heavy-hydrogenation content forming polymers which can be used as material for optical fibers capable of giving high transparency and low propagating-light loss. And another object of the present invention is to provide a process for producing heavy-hydrogenated norbornyl (meth) acrylates with low cost industrially.

In order to achieve the objects, the present invention provides a compound represented by a formula [1]:

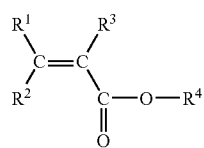

[1]

wherein $R^1$ and $R^2$ respectively represent a light or heavy hydrogen atom, $R^3$ represents a light or heavy hydrogen atom or a methyl group in which three hydrogen atoms are respectively light or heavy hydrogen atoms, and $R^4$ is a norbornyl group provided that four or more hydrogen atoms in the norbornyl group are heavy hydrogen atoms.

It is preferred that not less than five, more preferred not less than six of hydrogen atoms contained in a norbornyl group represented by $R^4$ are heavy-hydrogen atoms.

From another aspect, the present invention provides a process for producing a compound represented by the formula [1], comprising reacting a norborneol containing four or more heavy hydrogen atoms in its norbornyl group with a compound represented by a formula [2]:

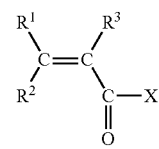

[2]

wherein $R^1$ and $R^2$ respectively represent a light or heavy hydrogen atom, $R^3$ represents a light or heavy hydrogen atom or a methyl group in which three hydrogen atoms are respectively light or heavy hydrogen atoms, and X represents a halogen atom, a hydroxyl group or an alkoxy group.

From another aspect, the present invention provides a polymer produced by polymerization of a composition comprising the compound represented by the formula [1]; the polymer in which 50% or more hydrogen atoms are heavy hydrogen atoms; an optical member comprising a region formed of the polymer; and the optical member which gives an absorbance at 910 nm being 70% or smaller percentage of that given by a polymer having a same structure except that all hydrogen atoms are light hydrogen atoms.

It will be noted that, in the specification, the term of "hydrogen atom" is a generic term for "light hydrogen atom" and "heavy hydrogen atom"; and the term of "heavy hydrogen atom" is used for deuterium (D) or tritium (T).

Further, in the specification, the term of "heavy-hydrogenation content" means a rate of a number of heavy hydrogen atoms to the total number of hydrogen atoms in a compound or a group.

DETAILED DESCRIPTION OF THE INVENTION

Figure 1:
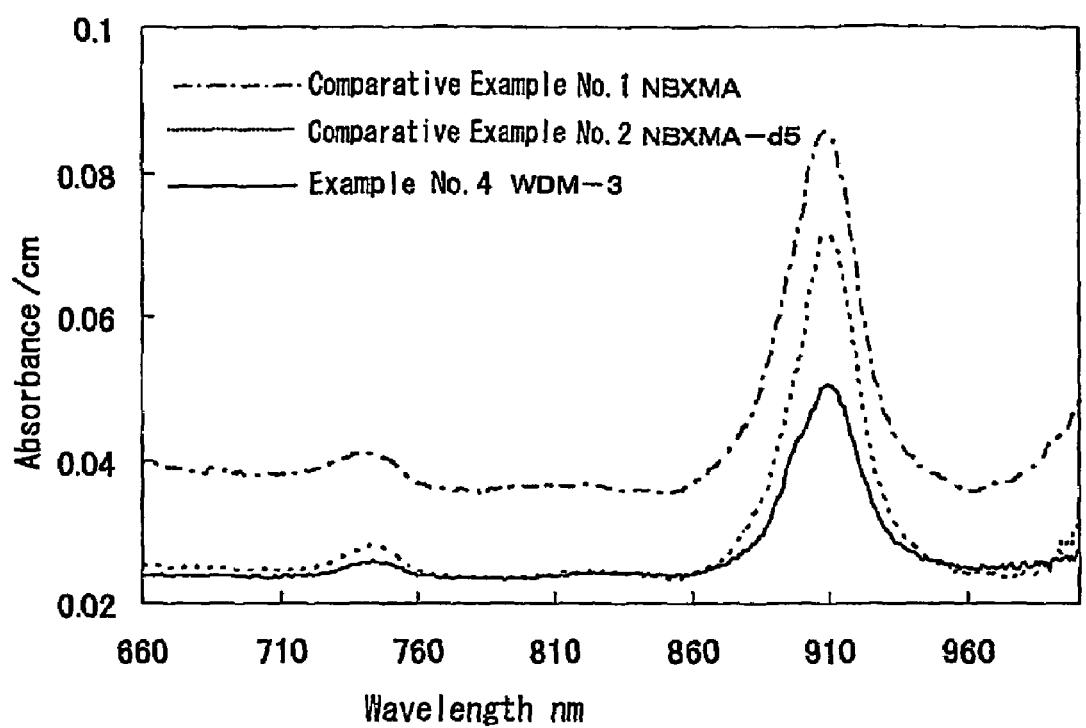
FIG. 1 is a graph showing near-IR absorption spectra determined for polymer rods of Example No. 4 and Comparative Example Nos. 1 and 2.

The embodiments of the present invention are described in detail bellow.

The present invention relates to compounds represented by a formula [1] below.

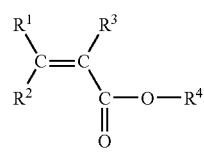

[1]

In the formula, $R^1$ and $R^2$ respectively represent a light or heavy hydrogen atom, $R^3$ represents a light or heavy hydrogen atom or a methyl group in which three hydrogen atoms are respectively light or heavy hydrogen atoms, and $R^4$ is a norbornyl group provided that four or more hydrogen atoms in the norbornyl group are heavy hydrogen atoms.

It is preferred that at least one of $R^1$ and $R^2$ is a heavy hydrogen atom, and more preferred that both of them are heavy hydrogen atoms.

When $R^3$ represents a hydrogen atom, a heavy hydrogen atom is preferred; and when $R^3$ represents a methyl group, at least one of three hydrogen atoms in the methyl group is desirably a heavy hydrogen atom, more desirably two of them are heavy hydrogen atoms and much more desirably all of them are heavy hydrogen atoms.

It is most preferred that $R^3$ represents a heavy-hydrogenated methyl group in which all of three hydrogen atoms are heavy hydrogen atoms.

Among the hydrogen atoms contained in the norbornyl group represented by $R^4$, desirably at least four or more, more desirably at least five or more and much more desirably at least six or more are heavy hydrogen atoms.

The norbornyl group represented by $R^4$ may have a substituent(s) selected from groups not having any C—H bonds such as a halogen atom, a trifluoromethyl group, a nitrile group and a carbonyl group.

The larger the number of heavy hydrogen atom in $R^1$, $R^2$ or $R^3$ is, the more desired it is; and it is most desired that all of hydrogen atoms in $R^1$, $R^2$ or $R^3$ are heavy hydrogen atoms.

The compound of the present invention can be produced by a process comprising reacting a norborneol containing four or more heavy hydrogen atoms in its norbornyl group with a compound represented by a formula [2]

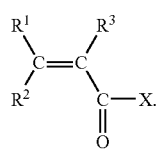

[2]

In the formula, each of $R^1$, $R^2$ or $R^3$ is same as each of them in the formula [1] and their preferred scopes are also same as those.

In the formula [2], X represents a halogen atom, a hydroxyl group or an alkoxy group. Examples of the halogen atom represented by X include a chlorine atom, a bromine atom, a fluorine atom or an iodine atom, among these, a chlorine atom or a bromine atom is preferred and a chlorine atom is especially preferred. The alkoxy represented by X may be linear, branched or cyclic, and is desirably selected from $C_{1-4}$ alkoxy groups, more desirably selected from $C_{1-2}$ alkoxy groups and much more desirably is a $C_1$ alkoxy group. Examples of the alkoxy group include a methoxy group, an ethoxy group, a propyloxy group, an isopropyloxy group, a butoxy group, an iso-butoxy group, a sec-butoxy group or a cyclopropyloxy group.

In the compound represented by the formula [2], compounds, having a larger ratio of a number of heavy hydrogen atoms to the total number of hydrogen atoms included in $R^1$, $R^2$ and $R^3$, are more desired. And compounds in which all of hydrogen atoms are heavy hydrogen atoms are most preferred.

It is to be noted that hydrogen atoms included in X may be light or heavy hydrogen atoms when X is a hydroxyl group or an alkoxy group.

The norborneol, which is used in the process of the present invention, having four or more heavy hydrogen atoms in its norbornyl group can be produced by carrying out reaction of a norborneol, in which all of or a part of hydrogen atoms are light hydrogen atoms, with heavy water under a light hydrogen gas atmosphere in the presence of palladium catalyst. It can also be produced by carrying out reaction of a norbornanone, in which all of or a part of hydrogen atoms are light hydrogen atoms, with heavy water under a light hydrogen gas atmosphere in the presence of palladium catalyst to heavy-hydrogenate norbornanone, and then carrying out reduction of the obtained heavy-hydrogenated norbornanone by using heavy-hydrogenated metal hydride such as heavy-hydrogenated lithium aluminium hydride and heavy-hydrogenated sodium boron hydride.

The compound represented by the formula [2] may be produced according to the known process described in JPA No. syo 63-130563 (1988-130563) or the like. Namely, the compound represented by the formula [1] may be produced by heavy-hydrogenation of a corresponding compound, in which all of or a part of hydrogen atoms are light hydrogen atoms, in heavy water in the presence of both of an alkaline earth metal salt and a polymerization inhibitor.

In the process of the present invention, when a compound represented by the formula [2] in which X is a halogen atom is used, the compound may be reacted with norborneol in the presence of a suitable base, if necessary in a suitable solvent. This embodiment will be referred to as "first embodiment" hereinafter.

According to the first embodiment, an amount of norborneol to be used is desirably from 0.8 to 1,000 times by mole, more desirably 0. 8 to 100 times by mole, much more desirably from 0. 8 to 50 times by mole and further much more desirably from 0. 8 to 10 times by mole of the compound represented by the formula [2].

The base which can be used in the first embodiment may be selected from bases which have been used in general esterifications of acid halide and alcohol. Examples of the base include organic amines such as triethylamine, N,N-dimethylaniline, piperidine, pyridine, 4-dimethylaminopyridine, N-methylmorpholine, 1,5-diazabicyclo[4.3.0]non-5-en, 1,8-diazabicyclo[5.4.0]undec-7-en and tri-n-butylamine; alkaline metal compounds such as sodium hydride and n-butyllithium, etc.

According to the first embodiment, an amount of the base to be used is desirably from 1 to 50 times by mole, more desirably from 1 to 20 times by mole and much more desirably from 1 to 5 times by mole of the compound represented by the formula [2].

Examples of the solvent to be used if necessary in the first embodiment include ethers such as diethylether, diisopropyl ether, ethyl methyl ether, tetrahydrofuran, 1,4-dioxane and dimethoxyethane; halogenated hydrocarbons such as chloromethane, methylene chloride, chloroform, carbon tetrachloride, dichloroethane, trichloroethane and chlorobenzene; hydrocarbons such as n-hexane, benzene, toluene and xylene; esters such as ethyl acetate, butyl acetate and methyl propionate; nitrites such as acetonitrile; amides such as N,N-dimethylformamide, etc. These solvents may be used alone or in a proper combination of two or more kinds thereof.

According to the first embodiment, a volume of the solvent to be used is desirably from 0 to 200 times, more desirably from 0 to 50 times and much more desirably from 0 to 20 times with respect to the volume of the compound represented by the formula [2].

According to the first embodiment, a reaction temperature is desirably from −20 to 200° C., more desirably from −20 to 100° C. and much more desirably from −10 to 70° C. A reaction time is desirably from 0. 5 to 200 hours, more desirably from 0. 5 to 36 hours and much more desirably from 0.5 to 12 hours.

In the process of the present invention, when a compound represented by the formula [2] in which X is a hydroxy group is used, the compound may be reacted with norborneol in the presence of a suitable dehydration condensing agent or acid catalyst, if necessary in a suitable solvent. The former process, in which a dehydration condensing agent is used, is referred to as "second embodiment" hereinafter; and the latter process, in which acid catalyst is used, is referred to as "third embodiment" hereinafter.

According to the second or third embodiment, an amount of norborneol to be used is desirably from 0.8 to 1,000 times by mole, more desirably 0.8 to 100 times by mole, much more desirably from 0.8 to 50 times by mole and further much more desirably from 0.8 to 10 times by mole of the compound represented by the formula [2].

The dehydration condensing agent which can be used in the second embodiment may be selected from agents which have been used in general dehydration condensing reactions; and examples of the dehydration condensing agent include inorganic dehydration agents such as diphosphorus pentaoxide and zinc chloride anhydride; carbodiimides such as dicyclohexyl carbodiimide, diisopropyl carbodiimide and 1-ethyl-3-(3-dimethylaminopropylcarbodiimide) hydrochloride; polyphosphoric acid, acetic anhydride, carbonyl diimidazole, p-toluenesulfonyl chloride, etc.

According to the second embodiment, an amount of the dehydration condensing agent to be used is desirably from 1 to 50 times by mole, more desirably from 1 to 30 times by mole and much more desirably from 1 to 10 times by mole of the compound represented by the formula [2].

Examples of the solvent to be used if necessary in the second embodiment include ethers such as diethylether, diisopropyl ether, ethyl methyl ether, tetrahydrofuran, 1,4-dioxane and dimethoxyethane; ketones such as acetone, dimethyl ketone, ethyl methyl ketone, diethyl ketone, 2-hexanone, t-butyl methyl ketone, cyclopentanone and cyclohexanone; halogenated hydrocarbons such as chloromethane, methylene chloride, chloroform, carbon tetrachloride, dichloroethane, trichloroethane and chlorobenzene; hydrocarbons such as n-hexane, benzene, toluene and xylene; esters such as ethyl acetate, butyl acetate and methyl propionate; nitriles such as acetonitrile; amides such as N,N-dimethylformamide, etc. These solvents may be used alone or in a proper combination of two or more kinds thereof.

According to the second embodiment, a volume of the solvent to be used is desirably from 0 to 100 times, more desirably from 0 to 50 times and much more desirably from 0 to 20 times with respect to the volume of the compound represented by the formula [2]).

According to the second embodiment, a reaction temperature is desirably from −20 to 100° C., more desirably from −20 to 80° C. and much more desirably from −10 to 50° C. A reaction time is desirably from 0.5 to 200 hours, more desirably from 0.5 to 36 hours and much more desirably from 0.5 to 12 hours.

Examples of the acid catalyst which can be used in the third embodiment include mineral acids such as hydrochloric acid, sulfuric acid and phosphoric acid anhydride; organic acids such as p-toluenesulfonic acid and ethane sulfonic acid; Lewis acids such as borontrifluoride etherate, etc.

According to the third embodiment, an amount of the acid catalyst to be used is desirably from 0.01 to 0.5 times by mole, more desirably from 0.01 to 0.2 times by mole and much more desirably from 0.01 to 0.1 times by mole of the compound represented by the formula [2].

Examples of the solvent to be used if necessary in the third embodiment include ethers such as diethylether, diisopropyl ether, ethyl methyl ether, tetrahydrofuran, 1,4-dioxane and dimethoxyethane; halogenated hydrocarbons such as chloromethane, methylene chloride, chloroform, carbon tetrachloride, dichloroethane, trichloroethane and chlorobenzene; hydrocarbons such as n-hexane, benzene, toluene and xylene, etc. These solvents may be used alone or in a proper combination two or more kinds thereof.

According to the third embodiment, a volume of the solvent to be used is desirably from 0 to 100 times, more desirably from 0 to 50 times and much more desirably from 0 to 20 times with respect to the volume of the compound represented by the formula [2].

According to the third embodiment, a reaction temperature is desirably from 0 to 200° C., more desirably from 20 to 200° C. and much more desirably from 20 to 150° C. A reaction time is desirably from 0.5 to 200 hours, more desirably from 0.5 to 36 hours and much more desirably from 0.5 to 12 hours.

And further, in the process of the present invention, when a compound represented by the formula [2] in which X is an alkoxy group is used, the compound may be reacted with norborneol in the presence of a suitable acid or base catalyst, if necessary in a suitable solvent. This embodiment will be referred to as "fourth embodiment" hereinafter.

According to the fourth embodiment, an amount of norborneol to be used is desirably from 0.8 to 1,000 times by mole, more desirably 0.8 to 100 times by mole, much more desirably from 0.8 to 50 times by mole and further much more desirably from 0.8 to 10 times by mole of the compound represented by the formula [2].

The acid or base catalyst which can be used in the fourth embodiment may be selected from catalysts which have been used in general ester-exchange reactions of ester and alcohol. Examples of the acid catalyst include sulfuric acid, p-toluenesulfonic acid, etc., and examples of the base catalyst include potassium t-butoxide, sodium methoxide, etc.

Examples of the solvent to be used if necessary in the fourth embodiment include ethers such as diethylether, diisopropyl ether, ethyl methyl ether, tetrahydrofuran, 1,4-dioxane and dimethoxyethane; halogenated hydrocarbons such as chloromethane, methylene chloride, chloroform, carbon tetrachloride, dichloroethane, trichloroethane and chlorobenzene; hydrocarbons such as n-hexane, benzene, toluene and xylene; nitriles such as acetonitrile; amides such as N,N-dimethylformamide, etc. These solvents may be used alone or in a proper combination of two or more kinds thereof.

According to the fourth embodiment, a volume of the solvent to be used is desirably from 0 to 100 times, more desirably from 0 to 50 times and much more desirably from 0 to 20 times with respect to the volume of the compound represented by the formula [2].

According to the fourth embodiment, a reaction temperature is desirably from 0 to 200° C., more desirably from 20 to 200° C. and much more desirably from 20 to 150° C. A reaction time is desirably from 0.5 to 200 hours, more desirably from 0.5 to 36 hours and much more desirably from 0.5 to 12 hours.

In any reaction as described above including the first to fourth embodiments, a polymerization inhibitor is preferably used for preventing the obtained compound represented by the formula [1] from polymerizing when the compound is purified from the reaction solution, since the compound represented by the formula [1] contains a polymerizable double bond in its molecular structure.

The polymerization inhibitor may be selected from agents which have been generally used as a polymerization inhibitor (an agent for preventing polymerization). Examples of the polymerization inhibitor include phenol type compounds such as p-methoxy phenol, t-butyl catechol, butyl hydroxy toluene and tetrakis [methylene 3-(3,5-di-tert-butyl-4-hydroxyphenyl)propionate]methane (trade name: Irganox 1010); hydroquinone type compounds such as hydroquinone, 2,5-bis(1,1,3,3-tetramethylbutyl) hydroquinone and 2, 5-bis (1,1-dimethylbutyl)hydroquinone; nitrosamine type compounds such as N-nitrosophenyl hydroxylamine and N-nitrosophenyl hydroxylamine aluminum salt; inorganic salts such as lithium bromide, etc. It is to be noted that an amount of the polymerization inhibitor to be used is desirably from 10 to 10,000 ppm and more desirably from 100 to 500 ppm with respect to the weight of the compound represented by the formula [1] to be obtained. When the compound of the present invention is used in production of optical fibers, it is afraid that the residue of polymerization inhibitor might cause worsening of light loss, especially light loss accompanied staining at a high temperature. Therefore, the polymerization inhibitor such as tetrakis [methylene 3-(3,5-di-tert-butyl-4-hydroxyphenyl)propionate]methane, which can be removed by a known method such as distillation or adsorption on columns is used desirably. An amount of the residue in terms of mass is desirably not greater than 50 ppm, more desirably not greater than 10 ppm and much more desirably not greater than 5 ppm as a standard for removing.

A homopolymer or a copolymer can be easily produced by carrying out polymerization of the compound, represented by the formula [1], of the present invention alone or with another monomer, since the compound of the present invention contains a polymerizable double bond in its molecular structure. Additives such as a polymerization initiator and a chain-transfer agent may be added to a reaction system of the polymerization reaction mentioned above in order to control polymerization conditions or properties of the polymer to be obtained. In this specification, the compound represented by the formula [1] itself or a mixture of the compound and the additives are called a polymerization composition.

A glass transition temperature (occasionally abbreviated to "Tg") of the polymers obtained by polymerization of one or more kinds of the compound represented by the formula [1] is desirably 100 to 130° C. and more desirably from 120 to 130° C.

In the compound of the present invention represented by the formula [1], not only all of or a part of hydrogen atoms in the groups represented by $R^1$, $R^2$ and $R^3$ but also four or more hydrogen atoms in the norbornyl group represented by $R^4$ are heavy-hydrogenated, and therefore, the polymer which can be obtained by polymerization of the compound of the present invention represented by the formula [1] has an excellent in transparency for a specific wavelength compared with a polymer obtained by polymerization of a corresponding compound in which all of or five or more hydrogen atoms in norbornyl represented by $R^4$ are light hydrogen atoms. As a rate of a number of heavy hydrogen atoms to the total number of hydrogen atoms (heavy-hydrogenation content) of the compound represented by the formula [1] gets higher, the transparency for a specific wavelength of a polymer obtained by polymerization of the compound is improved. It is to be noted that, in the specification, the term of "heavy-hydrogenation content" means a rate of a number of heavy hydrogen atoms to the total number of hydrogen atoms contained in a compound represented by the formula [1] or a polymer which can be obtained by polymerization of a compound represented by the formula [1]. The heavy-hydrogenation content of 0% means that all of hydrogen atoms contained in a compound or a polymer are light hydrogen atoms. And a natural abundance of a heavy hydrogen atom is 0.015%, and therefore, a heavy-hydrogenation content of any un-heavy-hydrogenated compound can be equated with 0%.

The compound represented by the formula [1], occasionally referred to as "the compound of the present invention", is useful as a labeled compound which can be used in various studies such as reaction mechanism studies and metabolic studies. And polymers obtained by polymerization of the compound of the present invention or by copolymerization of the compound of the present invention and another monomer are useful for various products such as optical members, resist materials and optical recording mediums, and are also useful for transparent products, since they are excellent in transparency. Examples of the optical member which can be produced by using the compound of the present invention include light guide elements, lenses for still cameras, video cameras, telescopes, glasses, contact lenses or solar collectors, concave mirrors, etc. Preferred examples are light guide elements and lenses.

Among the polymers, copolymers produced by copolymerization of the compound of the present invention and heavy-hydrogenated methyl methacrylate are remarkably useful as raw polymers for optical fibers. Copolymers produced by copolymerization of the compound of the present invention, heavy-hydrogenated methyl methacrylate and another monomer such as fluorine-containing monomer and a monomer having any functional groups, which can be used selected depending on the use of the copolymer, are also useful as raw polymers for optical fibers.

Taking optical fibers as one example, optical members, which are embodiments of the present invention, will be described hereinafter. One embodiment of the present invention relates to an optical fiber comprising a region formed of a polymer which is produced by using the compound of the present invention. The scope of this embodiment includes optical fibers comprising the region which has a uniform refractive index and the optical fiber comprising the region which has a graded refractive index. Optical fibers are classified according to the refractive index profile, into a so-called step index type plastic optical fiber (SI type POF), a so-called multi step index type plastic optical fiber (MSI type POF) or a so-called graded index type plastic optical fiber (GI type POF), and the compound of the present invention can be used for producing any types of optical fibers. Among these, from the viewpoint of optical fiber bandwidth, GI type POF is most preferred. It is known that the MSI type or GI type refractive index can be created by adding a dopant or by combining plural polymers having a different refractive index each other.

Being used for producing of optical members, especially optical fibers, transparent polymers are preferred. It is to be noted that, in the specification, the term of "transparent polymer" is used for any polymers having a transparency not less than 50%, desirably not less than 70% and much more desirably not less than 90%, against light. When the optical member is always used at a specific wavelength range, the polymer is not required to have a high transparency at all wavelengths.

The optical fibers formed of homopolymers or copolymers of the compound represented by the formula [1] are reduced in an absorption at about 910 nm attributed to the fourth overtone of C—H stretch vibration remarkably. In the case of the optical fibers used with a commercially available light of 850 nm (VCSEL), the bottom of the absorption at 910 nm may have an effect on transmitting light loss. The absorption at 910 nm of the optical fiber, which is formed of the above polymer, is significantly small, the effect of the absorption is small, and the optical fiber is thus reduced in transmitting light loss. It is preferred that absorption at 910 nm of the polymer is 50% or less of that of an un-heavy-hydrogenated polymer, or in other words a polymer having zero percentage heavy-hydrogenation.

The transparent polymers, which can be used as a material for optical fibers, can be produced by polymerization of the compound of the present invention alone, or copolymerization of the compound of the present invention and at least one unsaturated ethylene monomer. Examples of the unsaturated ethylene monomer, which can be copolymerized with the compound of the present invention, include acrylates, methacrylates, acrylamides, methacrylamides, maleimides, vinyl esters, vinyl ketones, allyl compounds, olefin acids, vinyl ethers, N-vinyl amides, vinyl hetero-ring compounds, maleates, itaconates, fumarates and crotonates. Among these, (meth) acrylates are preferred, methacrylates are more preferred and methyl methacrylate is especially preferred. Form the viewpoint of transparency of the polymer, it is preferred that these unsaturated ethylene monomers are heavy-hydrogenated. The copolymer, which can be produced by copolymerization of the compound of the present invention and heavy-hydrogenated methyl methacrylate, is extremely useful as material for optical fibers. The adequate copolymerization ratio may be decided in consideration of desired properties or types of monomers to be used.

When the transparent polymers are produced, the known polymerization initiators or the know chain transfer agents may be used in order to control the molecular weight of the polymer depending on types of target optical fibers. Preferred examples of the polymerization initiator and the chain transfer agent are described in International publication WO03/19252, and examples of them include peroxide compounds and azo compounds such as 2,2'-azobisisobutyonitrile, 2,2'-azobis (2-methylbutylonitrile), 1,1'-azobis(cyclohexane-1-carbonitrile), 2,2'-azobis(2-methylpropane), 2,2'-azobis(2-methylbutane), 2,2'-azobis(2-methylpentane), 2,2'-azobis(2,3-dimethylbutane), 2,2'-azobis(2-methylhexane), 2,2'-azobis(2,4-dimethylpentane), 2,2'-azobis(2,3, 3-trimethylbutane), 2,2'-azobis(2,4,4-trimethylpentane), 3,3'-azobis(3-methylpentane), 3,3'-azobis(3-methylhexane), 3,3'-azobis(3,4-dimethylpentane), 3,3'-azobis(3-ethylpentane), dimethyl-2,2'-azobis(2-methylpropionate), diethyl-2,2'-azobis(2-methylpropionate) or di-tert-butyl-2,2'-azobis(2-methylpropionate). The polymerization initiators which can be used are not limited to these, and two or more polymerization initiators may be used in combination. For satisfying requirements for various properties such as mechanical properties or transparency, the molecular weight of the polymer desirably falls within a range from 10,000 to 1,000,000. Polymerization of the compound of the present invention may be carried out according to various known polymerization methods such as solution polymerization, dispersion polymerization, bulk polymerization or emulsion polymerization, and from viewpoint of transparency, bulk polymerization is preferred. And the refractive index of the polymer may be controlled by addition of an agent for controlling refractive index, and according to a so-called interfacial gel polymerization, a refractive index profile varying along a desired direction can be created.

An ingredient for controlling refractive index is an ingredient which can give a higher refractive index in a polymer formed of a polymerizable composition when the ingredient is contained in the composition, compared with when the ingredient is not contained in the composition. The ingredient may be selected from high or low molecular weight compounds. The difference in refractive index, which is brought by addition of the ingredient, is desirably not less than 0.005. The ingredient such that a polymer containing the ingredient has a higher refractive index compared with a polymer not containing is preferred. The ingredient may be selected from polymerizable compounds. When an ingredient for controlling refractive index is polymerizable, it is preferred that the ingredient is selected from compounds which can give a higher refractive index to a copolymer containing the compound as a copolymer ingredient compared with a polymer not containing the compound. Any compounds which have the above mentioned properties, coexisting with a polymer and being stable under a polymerization condition of the compound of the present invention (such as a heating or pressurizing condition) can be used as an ingredient for controlling refractive index. Addition of the ingredient to the polymer enables the polymer to have the adequate value or the adequate profile of the refractive index depending on the application or the purpose of the polymer. For example, according to the method described in International publication WO03/19252, JPA No. 2003-75656, JPA No. 2003-149463 or the like, a core in which the refractive index is graded, can be produced by addition of the ingredient, and thus a GI-type plastic optical fiber, having a wide bandwidth, can be obtained.

Examples of the ingredient for controlling refractive index include low-molecular compounds such as benzyl benzoate (BEN), diphenyl sulfide (DPS), triphenyl phosphate (TPP), benzyl-n-butyl phthalate (BBP), diphenyl phthalate (DPP), biphenyl (DP), diphenylmethane (DPM), tricresyl phosphate (TCP) or diphenyl sulfoxide (DPSO). Among these, particularly preferable species are BEN, DPS, TPP and DPSO. Examples of the ingredient for controlling refractive index, which can polymerize with a compound represented by the formula [1], include benzyl methacrylate, phenyl methacrylate and bromophenyl methacrylate. In the present invention, hydrogen atoms in the ingredient are desirably replaced with heavy hydrogen atoms. For example, heavy-hydrogenated bromobenzene can be used for the purpose of improvement of transparency at wide wavelengths.

The refractive index may be set to a desired value by adjusting the concentration or the distribution of the ingredient, and the types or the additional amount of the ingredient may be decided depending on the applications. Tow or more types of compounds may be used as an ingredient for controlling refractive index.

The optical material or the optical member of the present invention may be produced by the various known method such as injection molding, compression molding, micromolding, floating molding, injection compression molding or cast molding. The various properties, such as moisture resistance, optical properties, chemical resistance, wear resistance or antifogging property, of the molded product may be improved by applying any coating treatment to the surface of the molded product.

EXAMPLES

The present invention will specifically be described referring to the specific examples. It is to be noted that any materials, reagents, ratio of use, operations and so forth can be properly altered without departing from the spirit of the present invention. The scope of the present invention is therefore by no means limited to the specific examples shown below.

Referential Example No. 1

Deuteration of 2-norbornanone

In 680 ml of deuterium oxide ($D_2O$) were suspended 40.0 g of 2-norbornanone and 4.0 g of palladium carbon (Pd 10%), and the atmosphere of the reaction system was replaced with hydrogen gas, followed by reacting for 24 hours at 180° C. in an oil bath. After the reaction was completed, n-hexane was added to the reaction solution, and then the catalyst was removed by filtration. After that, the filtrate was separated into two liquid layers, and then a solvent of the obtained organic layer was evaporated under reduced pressure to give 35.0 g of deuterated 2-norbornanone in an 85% yield.

Referential Example No. 2

Synthesis of Deuterated norborneol

In 150 ml of tetrahydrofuran anhydride were dissolved 35.0 g of deuterated 2-norbornanone produced by Referential Example No. 1, and the obtained solution was added dropwise to a suspension, which was prepared by suspending 4.6 g of deuterated aluminium lithium in 150 ml of tetrahydrofuran anhydride, on being cooled with ices under a nitrogen stream; and followed by reacting for two hours. After the reaction was completed, the reaction solution was left to stand overnight to give crystals. Dilute hydrochloric acid was added dropwise to the reaction solution until the crystals were dissolved, and after that, the reaction solution was extracted with ether. A solvent of the extraction was evaporated under reduced pressure to give 34.2 g of deuterated norborneol in a 96% yield. The structural analysis of the obtained deuterated compound was carried out by $^1$H-NMR and $^2$H-NMR measurements, and revealed that the average deuteration content of the obtained deuterated compound was 49%.

Referential Example No. 3

Deuteration of norborneol

In 340 ml of deuterium oxide ($D_2O$) were suspended 20.0 g of norborneol and 2.0 g of palladium carbon (Pd 10%) and followed by reacting for 24 hours at 180° C. in an oil bath. After the reaction was completed, n-hexane was added to the reaction solution, and then the catalyst was removed by filtration. After that, the filtrate separated into two liquid layers. A solvent of the obtained organic layer was evaporated under reduced pressure to give 11.8 g of deuterated norborneol in a 59% yield. The structural analysis of the obtained deuterated compound was carried out by $^1$H-NMR and $^2$H-NMR measurements, and revealed that the average deuteration content of the obtained deuterated compound was 51%.

Example No. 1

Synthesis of a Compound of the Present Invention

In 75 ml of dichloromethane were dissolved 28.8 g of deuterated norborneol, which was prepared by Referential example No.2, and 25.3 g of triethylamine ,and to the solution, 30.1 g of methacryloyl chloride, in which all hydrogen atoms were replaced with deuterium atoms, was added dropwise under cooling with ices, and the solution was then reacted for two hours at room temperature. After the reaction was completed, the crystals precipitated in the reaction solution were removed by filtration, and p-methoxyphenol was added to the obtained filtrate, followed by distillation under reduced pressure to give 35.2 g of deuterated norbornyl methacrylate in a 75% yield as a colorless oil having a boiling point of 61 to 65° C./1 Torr. The structural analysis of the obtained deuterated compound was carried out by $^1$H-NMR and $^2$H-NMR measurements, and revealed that the average deuteration content of the obtained deuterated compound was 66.8%. The compound is referred to as "WDM-3" hereinafter.

Example No. 2

Synthesis of a homopolymer

To 1.0 g of WDM-3 obtained by Example No. 1 was added 1 mg of dimethyl 2,2'-azobis(2-methylpropionate) (manufactured by Wako Pure Chemical Industries, Ltd.; trade name "V-601"), followed by polymerization for six hours under vacuum at 70° C. After the polymerization was completed, methanol was added to the reaction solution to give precipitates. The precipitates were separated from the solution by filtration and dried under reduced pressure to give 0.8 g of deuterated poly(norbornyl methacrylate) as white powder. The obtained polymer had a glass transition temperature of about 143° C.

Example No. 3

Synthesis of a copolymer

With 1.0 g of WDM-3 obtained by Example No. 1 was mixed 5.0 g of deuterated methyl methacrylate (MMA-d8), and 1 mg of dimethyl 2,2'-azobis(2-methylpropionate) (manufactured by Wako Pure Chemical Industries, Ltd.; trade name "V-601") and 1.5 mg of laurylmercaptan were added thereto, followed by polymerization for six hours under vacuum at 70° C. After the polymerization was completed, methanol was added to the reaction solution to give precipitates. The precipitates were separated from the solution by filtration and dried under reduced pressure to give 5.7 g of deuterated poly (norbornyl methacrylate/methyl methacrylate) as white powder. The obtained polymer had a weight-average molecular weight of 99,000 and a molecular weight distribution of 2.0. And the obtained polymer had a glass transition temperature of 115° C.

Example No. 4

A monomer, WDM-3 prepared by Example No. 1, dimethyl-2,2'-azobis(2-methylpropionate) of 0.14 wt % with respect to the weight of WDM-3 as a polymerization initiator and n-laurylmercaptan of 0.2 wt % with respect to the weight of WDM-3 were mixed to form a polymerizable composition. After being deaerated for 5 minutes with a stream of nitrogen, the polymerizable composition was polymerized for 24 hours at 7° C., 24 hours at 90° C. and further for 3 hours at 105° C. without being exposed to air to form a polymer rod.

The obtained polymer rod had both end portions cut off by a diamond cutter, and had the cut surface polished optically. It is referred to as Example No. 4. The near IR absorption spectrum of Example No. 4 was determined. The result was shown in FIG. 1.

Comparative Example Nos. 1 and 2

Two polymer rods (Comparative Example Nos. 1 and 2) were produced respectively in the same manner as Example No. 4, except that NBXMA-d5, wherein the total deuteration content was 31.3% and the deuteration content at side chain, or in other words at $R^4$ in the formula [1], was 0%, and NBXMA, wherein the total deuteration content was 0%, were used respectively in the place of WDM-3.

The near IR absorption spectra of Comparative Example Nos. 1 and 2 were measured in the same manner as Example No. 4. The results were also shown in FIG. 1.

The results shown in Fig.1 reveals that the polymer rod, which was produced by polymerization of the composition comprising WDM-3 falling within the scope of the present invention, gave a much smaller absorption attributed to the fourth C—H overtone at about 730 nm or about 910 nm compared with the polymer rod which was prepared by polymerization of the composition comprising the above comparative compound. The results suggests that when an optical fiber to propagate light emitted from a commercially available 850 nm-light source is produced by polymerization of a composition comprising WDM-3, the optical fiber exhibits a high transparency and low propagating-light loss because the bottom of the absorption band at 910 nm has little influence on propagating-light loss. Furthermore such an optical fiber has a high glass transition temperature and thus has a high thermostability. Accordingly, it is possible to produce transparent optical fibers having high thermostability and giving very low absorption attributed to C—H high frequency stretching by drawing the polymer into fiber in the same manner described in International publication WO03/019252 or the like.

INDUSTRIAL APPLICABILITY

According to the present invention, it is possible to provide heavy-hydrogenated compounds represented by the formula [1] with a high heavy-hydrogenation content, which can be produced from inexpensive starting material, and thus capable of being applied to industrial uses with advantage of cost. Being copolymerized with another monomer selected from various monomers, the heavy-hydrogenated compounds of the present invention can form polymers, having a high thermostability sufficient to be used even under severe conditions such as a high-temperature atmosphere, which can be used as a starting materials for optical fibers having a high transparency and low propagating-light loss to be used in high-capacity and high-speed transmitting systems.

The invention claimed is:

1. A process for producing a compound represented by a formula [1]:

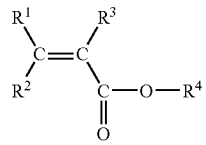

[1]

wherein $R^1$ and $R^2$ respectively represent a light or heavy hydrogen atom, $R^3$ represents a light or heavy hydrogen atom or a methyl group in which three hydrogen atoms are respectively light or heavy hydrogen atoms, and $R^4$ is a norbornyl group provided that four or more hydrogen atoms in the norbornyl group are heavy hydrogen atoms, comprising:

(i) reacting a norborneol with heavy water in the presence of palladium catalyst under an atmosphere of light hydrogen gas, or (ii) reacting a norbornanone with heavy water in the presence of palladium catalyst under an atmosphere of light hydrogen gas and then reducing the obtained deuterated norbornanone, thereby to obtain a deuterated norborneol containing four or more heavy hydrogen atoms in its norbornyl group; and reacting said deuterated norborneol with a compound represented by a formula [2]:

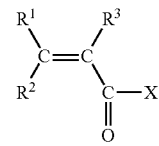

[2]

wherein $R^1$ and $R^2$ respectively represent a light or heavy hydrogen atom, $R^3$ represents a light or heavy hydrogen atom or a methyl group in which three hydrogen atoms are respectively light or heavy hydrogen atoms, and X represents a halogen atom, a hydroxyl group or an alkoxy group.

2. A process for producing a deuterated norborneol comprising:

(i) reacting a norborneol with heavy water in the presence of palladium catalyst under an atmosphere of light hydrogen gas, or (ii) reacting a norbornanone with heavy water in the presence of palladium catalyst under an atmosphere of light hydrogen gas and then reducing the obtained deuterated norbornanone.

* * * * *